United States Patent [19]

Chien et al.

[11] Patent Number: 4,806,341

[45] Date of Patent: Feb. 21, 1989

[54] TRANSDERMAL ABSORPTION DOSAGE UNIT FOR NARCOTIC ANALGESICS AND ANTAGONISTS AND PROCESS FOR ADMINISTRATION

[75] Inventors: Yie W. Chien, North Brunswick; Chin-Chih Chiang, Piscataway; Kabuji Tojo, Highland Park, all of N.J.

[73] Assignee: Rutgers, The State University of New Jersey, New Brunswick, N.J.

[21] Appl. No.: 903,273

[22] Filed: Sep. 3, 1986

Related U.S. Application Data

[63] Continuation-in-part of Ser. No. 705,194, Feb. 25, 1985, and a continuation-in-part of Ser. No. 770,968, Aug. 30, 1985.

[51] Int. Cl.$^4$ .............................................. A61F 13/00
[52] U.S. Cl. .................................... 424/448; 424/449
[58] Field of Search ........................ 414/448, 449, 409

[56] References Cited

U.S. PATENT DOCUMENTS

| | | | |
|---|---|---|---|
| 3,946,106 | 3/1976 | Chien et al. | 424/449 |
| 4,336,243 | 6/1982 | Sanvordeker et al. | 424/449 |
| 4,599,342 | 7/1986 | LaHann | 514/282 |
| 4,662,218 | 11/1986 | Bodor | 424/9 |
| 4,690,683 | 9/1987 | Chien et al. | 424/448 |

Primary Examiner—Thurman K. Page
Assistant Examiner—F. R. Horne
Attorney, Agent, or Firm—Leroy G. Sinn

[57] ABSTRACT

Transdermal absorption morphinan narcotic analgesic or antagonist pharmaceutical polymer matrix dosage units have been developed which comprise a backing layer and an adjoining layer of a solid polymer matrix in which minimum effective doses of morphinan narcotic analgesic or antagonist pharmaceuticals are microdispersed and transdermally supplied. A presently preferred analgesic is hydromoprhone. The dosage units use a biologically acceptable adhesive polymer means to adhere the dosage units to the subject to be treated. The polymer matrix has dispersed one or more skin permeation enhancers. The invention also provides a process for transdermal absorption of said pharmaceuticals in at least minimum dosage amounts.

25 Claims, 6 Drawing Sheets

TRANSDERMAL ABSORPTION DOSAGE UNIT FOR NARCOTIC ANALGESICS AND ANTAGONISTS AND PROCESS FOR ADMINISTRATION

This application is a continuation-in-part of both U.S. application Ser. No. 06/705,194, filed Feb. 25, 1985, by Yie W. Chien and Chia-Shun Lee and U.S. application Ser. No. 06/770,968, filed Aug. 30, 1985, by Yie W. Chien and Chia-Shun Lee.

TECHNICAL FIELD

This invention relates to a novel transdermal absorption dosage unit comprising a backing layer, an adjoining layer of solid polymer matrix in which a morphinan narcotic analgesic such as hydromorphone or a morphinan narcotic antagonist, such as naloxone, is microdispersed; and a biologically acceptable adhesive means by which the dosage unit adheres to the skin of the subject being administered said morphinan narcotic analgesic or morphinan antagonist and adapted to permit transdermal absorption thereof. Additionally, the invention relates to improved morphinan narcotic analgesic or antagonist therapy.

Hydromorphone and other morphinan narcotic analgesics are used to alleviate severe and chronic pain in patients such as those terminally ill with diseases such as various cancers. The morphinan narcotic antagonists are useful in blocking or offsetting the effects of administered narcotic analgesics of the morphine type.

BACKGROUND ART

It has been found that certain pharmaceuticals are absorbed to a degree through the skin. This is referred to as transdermal pharmaceutical absorption. One means of effecting transdermal absorption has been to distribute the pharmaceutical within a polymeric disc or a container of a gel, which is brought into contact with an area of the skin of the subject to be treated with the pharmaceutical. Also, ointments or lotions containing a desired pharmaceutical have been applied to an area of the skin of the subject to be treated. Problems encountered in such treatment include inadequate control over the rate and duration of transdermal absorption or the rate can be too slow in the case of certain dosage forms, especially from pharmaceutical-containing discs or pharmaceutical-containing gel container dosage units or pads. It has been found that the transdermal absorption rates of certain pharmaceuticals can be increased by use of absorption promoting compounds (also referred to as skin permeation enhancers) with the pharmaceutical to be absorbed when compounding the polymeric disc or the pharmaceutical-containing gel.

It is desired to improve the dosage unit forms or devices by which pharmaceuticals are transdermally absorbed, especially in view of the importance of administration of pharmaceuticals by this means. Desired transdermal absorption of pharmaceuticals would provide an avoidance of gastrointestinal incompatibility with the pharmaceuticals and unwanted destruction of the pharmaceutical by metabolism in the gastrointestinal tract and by a "first pass" hepatic metabolism. The transdermal absorption minimizes inter- and intra-patient variations regarding such incompatibilities and metabolisms. By transdermal absorption, it is deemed possible to provide more constant pharmaceutical concentration in the body and to realize a greater pharmaceutical efficiency. It is possible, by proper transdermal absorption, to reduce the frequency of effective dosing. Transdermal administration provides most of the advantages of intravenous dosing without the necessity of hospitalization and the accompanying discomfort and inconvenience.

With regard to specific pharmaceuticals to which this invention is directed, the morphinan narcotic analgesic hydromorphone is an illustration of a morphinan narcotic analgesic or antagonist pharmaceutical in which great loss of orally administered pharmaceutical occurs by first-pass through the liver. Therefore, oral administration of hydromorphone is a deficient means of administering hydromorphone as well as other morphinan narcotic analgesics and antagonists. Hydromorphone and other of the morphinan narcotic analgesics and antagonists can also be administered parenterally, but this method has the disadvantages of the discomfort and unpleasantness of injection as well as the hazards of injection. Hydromorphone and other of the morphinan narcotic analgesics and antagonists can be administered nasally according to U.S. Pat. No. 4,464,378.

There is clearly a need for improvements in means and methods for morphinan narcotic analgesic and antagonist therapy. Such a need could be provided by effective transdermal dosage unit forms and therapy processes, especially in view of the ease and convenience of administration and cessation of therapy.

SUMMARY OF INVENTION

This invention relates to an improved transdermal pharmaceutical-containing dosage unit comprising:

(a) a backing layer which is substantially impervious to the pharmaceutical to be delivered transdermally;

(b) a polymer matrix disc layer which is in contact with said backing layer and which has microdispersed therein an amount of pharmaceutically acceptable morphinan narcotic analgesic or antagonist are capable of transdermal absorption, said disc layer providing a dosage amount of the said morphinan narcotic pharmaceutical to be delivered transdermally; and (c) an adhesive means which adheres the dosage unit in intimate contact with the skin of the subject being treated to permit the morphinan narcotic pharmaceutical to be absorbed transdermally.

The backing layer is made from materials that are substantially impermeable with regard to the morphinan narcotic pharmaceutical of the transdermal dosage unit. It can be made of polymers such as polyethylene, polypropylene, polyvinylchloride, polyurethane, polyesters such as poly(ethylene phthalate), and foils such as laminates of polymer films with metallic foils such as aluminum foil.

The polymer matrix disc layer is suitably fabricated from biologically acceptable lipophilic polymers. The polymer matrix disc layer which has the morphinan narcotic pharmaceutical distributed therein can suitably be made of a medical-grade silicone polymer such as a polydimethylsiloxane polymer. The silicone polymer can also be a block or graft or other type copolymer. The morphinan narcotic pharmaceutical is suitably dispersed in the silicone polymer, to which mixture a curing agent is suitably added. The polymer-narcotic pharmaceutical mixture is then formed into a layer of an appropriate thickness and suitable surface area and is cured, if desired. The matrix layer is adhered to the backing layer. Other suitable polymers which can be used in the formulation of the polymer matrix disc layer are elastomers or thermoplastics. Care must be taken that the polymer selected is compatible with the morphinan narcotic pharmaceutical, permits its release for transdermal absorption and is free or sufficiently free from any biologically unacceptable components.

A suitable morphinan narcotic analgesic used in formulating the polymer matrix disc layer is commonly hydromorphone. Other morphinan narcotic analgesics and antagonists can be used which are biologically compatible and can be absorbed effectively transdermally. The morphinan narcotic analgesics and antagonists contemplated for use in this invention are described under the DETAILED DESCRIPTION OF THE INVENTION AND THE PREFERRED EMBODIMENTS section. In formulating the polymer disc layer, it is desirable at times to utilize two or more compatible pharmaceuticals, such as in combination with hydromorphone.

Finally, the adhesive means of the dosage unit is assembled with the other layer elements to form the dosage units. The adhesive means selected can vary depending on many factors including economic factors such as the type of manufacturing equipment most readily available, the rapidity of absorption desired or other factors. For example, the adhesive layer can be applied directly to the polymer matrix disc layer or to the backing layer if it is adapted to extend around the sides of the matrix layer and then outwardly to provide a ring surface for an adhesive ring or the adhesive means can be a separate overlay means which is adapted to be applied over the backing layer to hold the matrix layer in intimate contact with the skin of the subject being treated. A skin permeation enhancer compound can be mixed thoroughly with the adhesive polymer which is suitable for adhesion to the skin locus to which the transdermal matrix dosage unit will be applied, if the adhesive layer is applied to the surface of the matrix layer. The adhesive polymer-skin permeation enhancer layer can be applied to the polymer matrix disc layer by spraying or by solvent casting or laminating. The concentration of skin permeation enhancer compound, if employed, can be reduced in the portion of the adhesive layer means, especially if less than desired adhesion is realized in the adhesive layer, by applying the surface portion of the adhesive layer separately wherein the adhesive composition has a lower concentration of skin permeation enhancer compound. The adhesive layer is desirably thin in the micron-range thickness, suitable 10–200 microns in thickness, desirably about 20 to 180 microns, and preferably about 30 to 150 microns in thickness. An effective amount of a skin permeation enhancer compound can also be incorporated into the pharmaceutical-containing disc layer. Also, if desired, the adhesive means can be in the form of a ring adhered to the backing layer which extends beyond the circumference of the disc layer. When such a concentric ring adhesive means is employed, the exposed surface of the pharmaceutical-containing matrix disc layer is held in intimate contact with the skin of the subject treated.

The absorption rate of the transdermal pharmaceutical absorption dosage units of the invention can be increased, such as by having an Enhancing Factor of at least 1.2, preferably at least 1.3, and more preferably at least about 1.5. Enhancing Factor is defined as the ratio of normalized permeation rate [in mcg/cm$^2$/hr] of a dosage unit of this invention with skin permeation enhancer/the normalized permeation rate of a corresponding dosage unit without enhancer.

The invention also is a process for administering said pharmaceutical transdermally by forming pharmaceutical-containing polymer matrix disc dosage unit having a polymer matrix disc layer which has the pharmaceutical dosage dispersed therein, to which matrix disc is adhered a backing layer, said dosage unit having assembled therewith an adhesive means, either a separate overlay means or an adhesive layer means adhered to the backing or matrix layer, to hold the dosage unit in intimate contact with the skin of the subject treated so that the pharmaceutical is absorbed transdermally, and by applying said dosage unit by way of said adhesive means to the skin of the subject to be treated, whereby said pharmaceutical is transdermally administered to said subject to achieve systemic effects.

DETAILED DESCRIPTION OF THE INVENTION AND THE PREFERRED EMBODIMENTS

Figure 1:
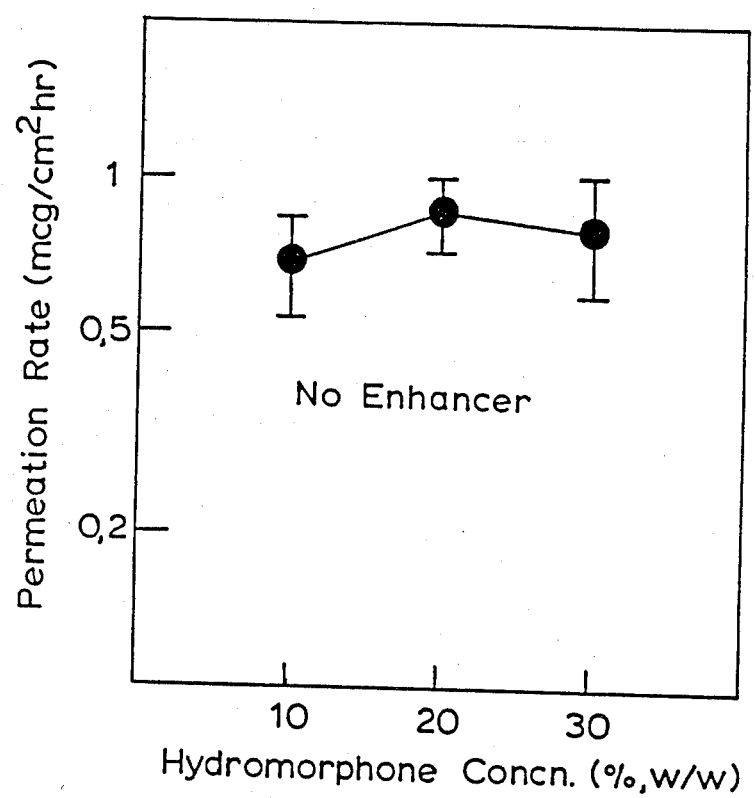
FIG. 1 is a graph showing permeation rates (mcg/cm$^2$ hr) at various hydromorphone loading doses (%, w/w) in polymer matrix dosage units in which no skin permeation enhancer is used.
Figure 2:
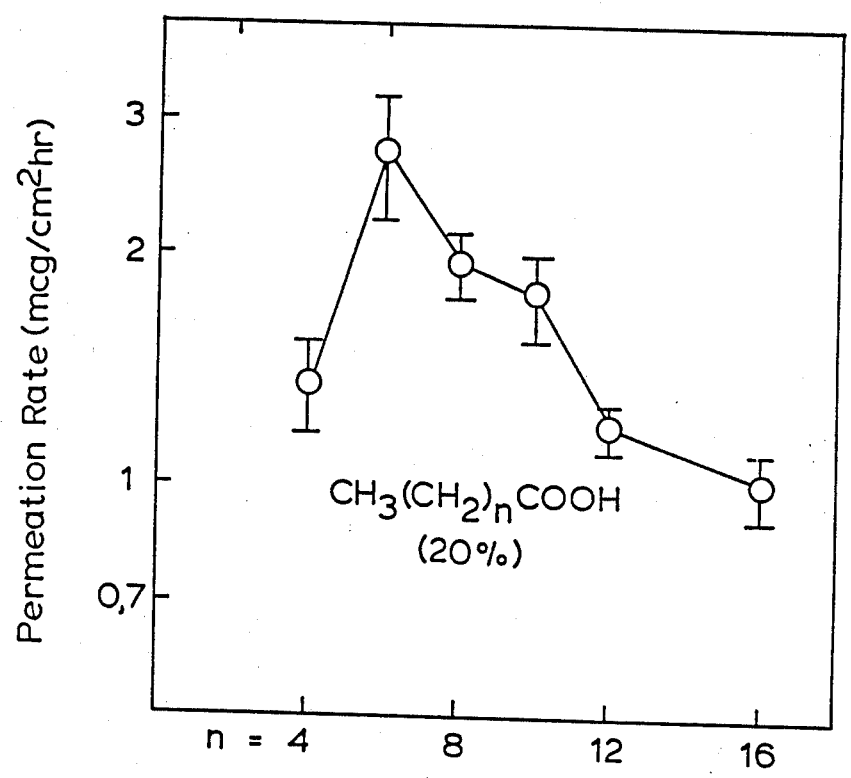
FIG. 2 is a graph showing permeation rates (mcg/cm$^2$ hr) from a dosage unit in which the polymer matrix layer has 10% hydromorphone concentration (w/w) and 10% of skin permeation enhancing agents of the formula $CH_3(CH_2)_nCOOH$ where n varies from 4 to 16.

The backing layer can be made of any suitable material which is impermeable to the pharmaceutical of the polymer matrix layer. The backing layer serves as a protective cover for the matrix layer and provides also a support function. The backing can be formed so that it is essentially the same size layer as the pharmaceutical-containing matrix disc layer or it can be of larger dimension so that it can extend beyond the side of the matrix disc layer or overlay the side or sides of the pharmaceutical-containing disc layer and then can extend outwardly in a manner that the surface of the extension of the backing layer can be the base for an adhesive means. The adhesive means holds the dosage unit in intimate contact with the skin of the subject treated. Examples of materials suitable for making the backing layer are films of high and low density polyethylene, polypropylene, polyvinylchloride, polyurethane, polyesters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the polymer matrix layer. The backing layer can be any appropriate thickness which will provide the desired protective and support functions. A suitable thickness will be from about 10 to about 200 microns. Desirably, the thickness will be from about 20 to about 150 microns, and preferably be from about 30 to about 100 microns.

The polymer matrix layer can be made from silicone elastomers of the general polydimethylsiloxane structure, such as silicone polymers of the following general formula:

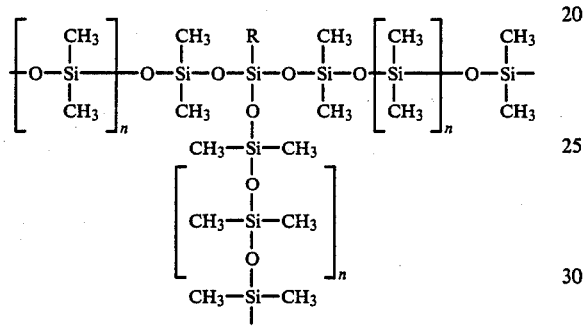

wherein R is alkyl or alkoxy containing 1-7 carbon atoms, vinyl or phenyl and wherein n is about 100 to about 5000.

The silicone polymers selected preferably are cross-linkable at moderate temperatures such as room temperature, using cross-linking catalysts which are biologically acceptable in the final polymer matrix and which are compatible with the pharmaceutical component to be used in making the polymer matrix dosage forms. Various suitable crosslinking agents can be used in crosslinking the above polymer such as tetrapropoxy silane [Si(OCH$_2$ CH$_2$ CH$_3$)$_4$] if the silicone polymer has free hydroxy groups such as terminal hydroxy groups. A tin catalyst can be used for such crosslinking reaction. If a silicone polymer component has vinyl groups, it can be crosslinked with a dimethyl-silicone polymer using a catalyst such as a platinum catalyst. Some suitable silicone polymers are cross-linkable copolymers having dimethyl and methylvinyl siloxane units, which can be crosslinked as by using a suitable peroxide catalyst. Other cross-linking sites can be present in the polysiloxane elastomers used. Suitable silicone medical-grade polymers are sold under the designations Silastic 382, Q7-4635, Q7-4650, Q7-4665, Q7-4735, Q7-4750, Q7-4765 and MDX-4-4210.

The silicone polymers selected can also have a "block" or "graft" structure or both. By "block" structure is meant that the polymer can have a section or block of the polymer chain structure of the polymer which can have a repeating unit of one type, such as dimethylsiloxane, and then have a succeeding block made up of repeating units of another type, such as methylvinylsiloxane, diphenylsiloxane, diisopropyl siloxane units or other siloxane or silane units or even of monomer units of a compatible non-siloxane or non-silane type. The blocks can vary in length and be repeated as desired. For example, if the blocks are represented as "A" and "B", respectively, the block copolymer can be A-B or A-B-A or A-B-A-B, etc. The "graft" structure simply means that to the main polymer chain, one or more polymer chains are attached. Those grafted chains can have the same polymer units as those of the main chain or can be different, as described above in connection with "block" copolymers. Also, the polymer used can be of a different type wherein copolymerizable monomers are placed together in a polymerization reactor so the main chain can have a certain population of each of the monomeric units.

The following are examples of block copolymers of the type which can be utilized in this invention.

"A" Block

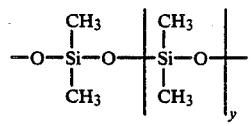

"B" Block

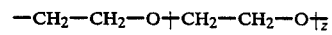

or

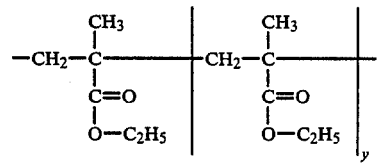

wherein y and z represent the number of repeating units sufficient to provide the desired property in the polymer, such as from about 10 to about 5000.

Generally, those polymers used to form the biologically acceptable polymer matrix are those capable of forming thin walls or coatings through which pharmaceuticals can pass at a controlled rate. Suitable polymers are biologically and pharmaceutically compatible, non-allergenic and insoluble in and compatible with body fluids or tissues with which the device is contacted. The use of soluble polymers is to be avoided since dissolution or erosion of the matrix would affect the release rate of the pharmaceutical as well as the capability of the dosage unit to remain in place for convenience of removal.

Exemplary materials for fabricating the biologically acceptable polymer matrix include polyethylene, polypropylene, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, chlorinated polyethylene, polyvinyl chloride, vinyl chloride-vinyl acetate copolymer, polymethacrylate polymer (hydrogel), polyvinylidene chloride, poly(ethylene terephthalate), butyl rubber, epichlorohydrin rubbers, ethylene-vinyl alcohol copolymer, ethylene-vinyloxyethanol copolymer; silicone copolymers, for example, polysiloxane-polycarbonate copolymers, polysiloxane-polyethyleneoxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxaneethylenesilane copolymers), and the like; cellulose polymers, for example methyl or ethyl cellulose, hydroxypropyl methyl cellulose, and cellulose esters; polycarbonates; polytetrafluoroethylene; and the like. For best results, the biologically acceptable polymer matrix should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after microdispersing the pharmaceutical into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

The adhesive means is suitably made in the form of a layer covering the pharmaceutical-containing disc and using a silicone adhesive, such as a polydimethylsiloxane adhesive depicted by the following formula:

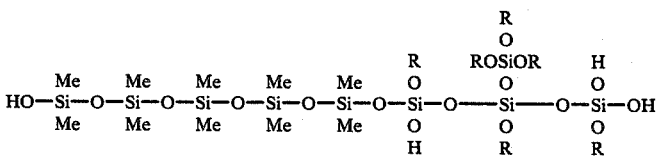

wherein Me is methyl and R is Si(CH$_3$)$_3$.

For example, adhesive products or amine-resistant adhesive products sold by Dow Corning, such as the one sold under the designation DC-355, are suitable for use in making the adhesive layer. The adhesive polymer must be biologically acceptable and compatible with the pharmaceutical and skin permeation enhancer, if used. Certain polyacrylic adhesive polymers (in the form of an alkyl ester, amide, free acid, or the like) or polyisobutylene adhesive polymers can also be used with some pharmaceuticals. Other suitable hypoallergenic pressure-sensitive contact adhesive compositions can be used. A preferred adhesive layer is pressure-sensitive.

However, if desired depending upon economic and other factors, the adhesive means can be in the form of a ring attached, for example, to an extended portion of the backing layer so that the adhesive layer is adjacent to the sidewall of the pharmaceutical-containing disc layer. The width of such adjacent adhesive ring must be adequate to hold the dosage unit securely to the subject being treated. Ordinarily, a suitable width of such adhesive ring can be about 0.2 to about 1.2 cm, preferably about 0.3 to about 1.0 cm.

The adhesive means then is finally covered in conventional therapeutic practice with a releasable or peelable protective film layer which is made from materials which are substantially impermeable to the pharmaceutical, the skin permeation enhancer if used and any other components of the polymer matrix dosage unit. The polymer materials and metal foil laminates used for the backing layer can be used to make the protective layer, provided the layer is made strippable or releasable such as by applying conventional siliconizing. A suitable releasable material for use with silicone polymer adhesive DC-355 is Scotchpak 1022 material sold by the 3 M Company.

The adhesive means, as referred to above, can be a separate overlay adhesive means, which can be made of a suitable polymer, laminate, or other material which has an adhesive layer. The adhesive is covered with a peelable layer for the purpose of therapeutic cleanliness. It is removed and discarded just prior to use of the overlay adhesive means to apply and adhere the polymer matrix layer to the skin in treatment.

In making the pharmaceutical-containing polymer matrix disc layer, silicone elastomers such as polydimethylsiloxane of the formula described above can suitably be used. In making the morphinan narcotic pharmaceutical-dispersed polymer matrix disc dosage units, it has been found suitable to use a polyol such as polyethylene glycol as a dispersing agent. Other suitable dispersing agents can be used instead so long as they are effective. Water-soluble polyols are generally suitable. For example, polyethylene glycols, such as those having a molecular weight of about 400, can be used, the molecular weight being variable therefrom, such as suitably between 300 and 500. Other suitable dispersing agents known to the formulating art can be used. Depending upon the morphinan pharmaceutical and the drug loading desired, a suitable amount of a dispersing agent can be varied from zero to about 50 percent (by weight) based on the weight of the polymer matrix disc. Commonly, the polyol is added as an aqueous solution with the polyol content varying from 10 to about 50 percent, based on the weight of the final polymer matrix. Aqueous solutions having about 40 percent polyol ordinarily are suitable, with some variation depending upon the rate of permeation desired, the particular morphinan narcotic analgesic or antagonist pharmaceutical used, and at times, other factors. The combination pharmaceutical and dispersing agent then is added to the polymer used to make the matrix disc layer. The amount of the pharmaceutical added depends upon the amount of pharmaceutical dosage desired in each dosage unit and the amount which can be incorporated into the polymer matrix disc to retain suitable structural, diffusion and other properties in the final matrix disc. It has been found, for example, that if the morphinan pharmaceutical is the analgesic hydromorphone, the amount of the pharamceutical which is suitable in making the polymer matrix is 10 percent based on the polymer weight. However, more can be added, such as 20–30 percent. It has been found suitable to dissolve and disperse the pharmaceutical used in an amount of a selected aqueous solution of polyol, such as PEG 400, or other dispersing agent. Also, one or more skin permeation enhancing agents can be incorporated and preferably are added to the polymer to form drug microreservoirs. At times, the skin permeation enhancing agent can also be used as the dispersing agent, for example, ethyl caprylate or combinations of ethyl caprylate with other skin permeation agents, such as capryl alcohol. Preferably, an effective amount of one or more skin permeation agents are thoroughly mixed with the polymer. For example, it has been found efficacious to add about 2 to about 50 precent or more of a suitable skin permeation enhancing agent or combinations thereof, based on the polymer weight, depending upon the polymer, pharmaceutical and skin permeation enhancing agents used. Ordinarily, the use of about 5 to about 50 percent based upon the polymer weight is suitable.

The polymer and pharmaceutical or pharmaceutical-dispersing solution are then thoroughly mixed using a high-torque mixer to form a homogeneous microdispersion of the pharmaceutical in the polymer. With continued agitation, an amount of cross-linking catalyst is desirably added together with a relatively low molecular weight polymer having a compatible chemical structure. For example, when polydimethylsiloxane based polymer is used as the polymer, a relatively low molecular weight polydimethylsiloxane and a cross-linking catalyst is added (such as 10 parts by weight of the low molecular weight polydimethylsiloxane and 30 drops of stannous octanoate per 100 g. amount of the final polydimethylsiloxane-pharmaceutical mixture) to the above illustrative composition of 20 parts of pharmaceutical dispersion and 70 parts of polydimethylsiloxane polymer. Again, the mixture is agitated with a high-torque mixer to form a uniform admixture. After each mixing step, the composition is subjected to vacuum to remove entrapped air.

The deaereated mixture is then placed in a device maker and heated to a suitable elevated temperature to promote cross-linking. A suitable temperature for cross-linking when the polymer used is polydimethylsiloxane of the above formula and the cross-linking catalyst is stannous octanoate, is from about 10° C. to about 200° C., desirably about 20° C. to about 100° C. The temperature used should not cause significant degradation of the pharmaceutical. The polymer matrix sheet desirably is about 0.05 to 5 mm, preferably about 0.1 to about 3 mm in thickness. The resulting cross-linked polymer matrix sheet is removed from the device maker and can be cut to form discs with desired shapes and sizes. The discs are then attached to a backing sheet, as described above, using an adhesive. The disc alternatively can be made directly on the backing sheet used. The discs generally should not exceed about 100 sq. cm in area, suitably about 5 to 100 sq. cm, preferably, about 8 to about 80 sq. cm, generally about 10 to 60 sq. cm being more preferable. The shape of the discs can vary; they can be circular, square, rectangular or other desired shape.

The pharmaceutical-containing polymer matrix disc layer, generally speaking, should contain some excess of the dispersed pharmaceutical over the dosage amount desired to be transdermally absorbed by the subject to be treated. Ordinarily, this excess is small, such as less than 2-fold excess. Generally speaking, an amount of the pharmaceutical used, which is sufficient, is less than 2 to about 10 times the desired dosage to about less than 2 to 5 times the desired dosage to be transdermally absorbed being adequate, depending upon the physiochemical properties of the pharmaceutical, as well as the nature of the polymer of the matrix disc layer and other factors.

The adhesive means if it contains a skin permeation enhancer is made as by dissolving the enhancer compound in a solvent for the enhancer which is compatible with the adhesive polymer solution used to make the adhesive layer containing the skin permeation enhancer.

Any suitable amount of solvent can be used as necessary to dissolve the quantity of enhancer to be admixed with the adhesive polymer solution used. For example, 3 to 10 parts of solvent can be used to dissolve one part of skin permeation enhancer, depending upon the solubility of the enhancer. When using polydimethylsiloxane adhesive solution, it has been found suitable to use 2 to 20 parts of skin permeation enhancer in 20 to 50 parts of solvent (such as acetone, methyl ethyl ketone, trifluorotrichloroethane or other suitable solvent) and add the solution to 100 parts of the adhesive solution. The enhancer - adhesive combination is thoroughly mixed and a coating thereof is applied using a film coating machine, directly onto the polymer matrix or to a strippable release liner before laminating onto the polymer matrix, as described above. A suitable release liner is a poly(ethylene phthalate) laminated with aluminum foil or a Tefloncoated polyester film such as sold under the designation Scotchpak 1022. The poly(ethylene phthalate) side to which the adhesive - enhancer coating is applied, is made strippable by conventional siliconizing or by other suitable means. The thickness of the adhesive - enhancer layer normally is suitable about 10 to about 200 microns, preferably about 30 to about 150 microns. The amount of enhancer in the adhesive layer depends in part on the rapidity at which it is desired that the pharmaceutical be absorbed. Generally speaking, about 1 to about 30 percent of skin permeation enhancer based on the weight of the adhesive is suitable depending upon the enhancer, adhesive polymer, desired adhesiveness and other factors. Desirably, about 5 to about 20 percent of skin permeation enhancers are used depending upon the above recited factors. The adhesive layer containing the skin permeation enhancer is transferred to the polymer matrix disc surfaces by application of lamination technique under a constant pressure. Preferably, in order to assure aedquate adhesion of the adhesive polymer layer to the skin of the subject treated, an enhancer-adhesive polymer solution having a relatively low concentration of enhancer, e.g., 1–2 percent based on the weight of the adhesive polymer is used to apply a coating to the release liner. The thickness of this coating ordinarily is a minor percentage of the thickness of the final adhesive layer, such as 20–40 percent of the total adhesive polymer layer. The remainder of the adhesive polymer layer having a suitable higher concentration of the enhancer is used to coat the matrix disc layer. Suitable higher concentratons of enhancer are usually 10 to about 30 percent based on the adhesive polymer weight, the solubility and desired final amount of skin enhancer agent and other factors. The solvent of the respective coatings is removed by evaporation. The respective coatings are combined to make the final adhesive polymer-enhancer agent layer by application of constant pressure.

The four-layer transdermal pharmaceutical polymer matrix dosage units are excised. The backing layer as desired can be shaped around the sides of the dosage unit including the polymer matrix layer if such protection is desired. The resulting pharmaceutical polymer matrix dosage unit forms are then placed in appropriate packaging for storage until they are to be applied in transdermal treatment.

At least one morphinan narcotic analgesic or antagonist is dispersed in the polymer matrix disc layer. The type of narcotic pharmaceutical which may be dispersed in the polymer matrix disc layer includes any morphinan narcotic pharmaceutical which is capable of being transdermally or topically administered to a subject to be treated and which is biologically acceptable. With the controlled release of the morphinan narcotic pharmaceutical at a relatively steady rate over a prolonged period, typically 24 hours or longer, the patient is provided with the benefit of a steady infusion of the morphinan narcotic pharmaceutical over a prolonged period. Ordinarily, it is desirable that about 2 to about 10 mg of hydromorphone be transdermally delivered to the subject being treated. About 5 mg has often been found to be a satisfactory oral dosage. It is believed that a lesser amount transdermally absorbed will be equally effective. Assuming that a 10 cm$^2$ dosage unit is used, it is desired that the rate of transdermal absorption will be at least about 5 mcg/cm$^2$ hr (about 1.2 mg daily dosage), preferably about 10 to about 50 mcg/cm$^2$ hr (about 2.4 to about 12.0 mg daily dosage). The amount transdermally delivered will be adjusted depending upon the daily dose desired and the morphinan narcotic pharmaceutical used and the subject being treated.

At times it will be desired to use a combination of the morphinan narcotic pharmaceutical in a single dosage unit, such as a morphinan-pharmaceutical which has analgesic activity as well as one that has antagonist activity. This can be desirable for several reasons, including the safety of dispensing.

The narcotic analgesics, narcotic antagonists and narcotic agonist-antagonists intended for use in the compositions and method of the present invention include morphine and pharmacologically active analogues thereof having at least one aromatic ring, said ring bearing at least one free OH group. Particularly significant morphine analogues contemplated by the present invention include analgesics such as the following: hydromorphone, levorphanol, methopon, and oxymorphone; and narcotic antagonists and agonist-antagonists such as buprenorphine, diprenorphine, butorphanol, levallorphan, nalorphine, naloxone, nalbuphine, oxilorphan, nalmexone and naltrexone. Other analogues contemplated by the invention included ketobemidone, apocodeine, profadol, cyclorphan, cyprenorphine, desomorphine, dihydromorphine, 3-hydroxy-N-methylmorphinan, levophenacylmorphan, norlevorphanol, oxymorphone, phenomorphan, pholcodine and hydroxypethidine. Especially preferred morphine analogues are those having antagonist or agonist-antagonist properties, especially naloxone, nalbuphine, naltrexone, buprenorphine and butorphanol. A pharmaceutically acceptable form of morphine or of its phenolic analogues is the free base form or any other pharmaceutically acceptable form which can be transdermally administered. Apomorphine can also be used. Chemical names of compounds above referred to include the following:

morphine: 7,8-didehydro-4,5 alpha-epoxy-17-methylmorphinan-3,6 alpha-diol
codiene: 7,8-didehydro-4,5 alpha-epoxy-3-methoxy-17-methylmorphinan-6 alpha-ol
hydrocodone: 4,5 alpha-epoxy-3-methoxy-17-methylmorphinan-6-one
hydromorphone: 4,5 alpha-epoxy-3-hydroxy-17-methylmorphinan-6-one
oxymorphone: 4,5 alpha-epoxy-3,4-dihydroxy-17-methylmorphinan-6-one
levorphanol: 17-methylmorphinan-3-ol The structural formulae for free bases of morphine, oxymorphine and hydromorphone are set forth below, some other narcotic analgesics and antagonists encompassed by this invention are shown in U.S. Pat. No. 4,464,378, Columns 3-6:

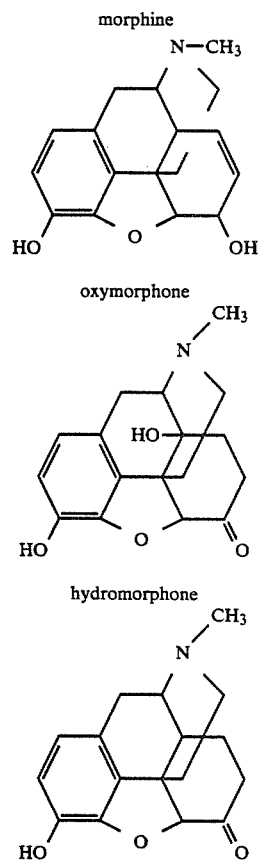

Morphine and its analogues can be prepared by well-known methods. Morphine itself can of course be isolated from natural sources and then converted, if desired, into a pharmaceutically acceptable acid addition salt.

It will be appreciated that the pharmaceutical may be added to the above mixture not only in the form of the pure chemical compound, but also in admixture with other pharmaceuticals which may be transdermally applied or with other ingredients which are not incompatible with the desired objective of transdermally administering the pharmaceutical to a patient.

Another group of compounds having narcotic analgesic or antagonist activity come within the group having an "azocine" function, such as cyclazocine, pentazocine, phenazocine, alazocine, metazocine, and the like which will be suggested to those skilled in the art. The particular compounds selected will depend upon its activity, pharmaceutical acceptability, transdermal absorbability, and other factors. The dosage used will depend upon the particular compound selected. Ordinarily, the dosage will be somewhat less than the amount found to be a satisfactory oral dose. The dosage units will be made in a manner following the above description. The method of therapy using these compounds will be in general accordance to the description herein set forth.

The skin permeation enhancers which can be used in carrying out this invention can vary. Ones that give preferred results with the polymer matrix dosage unit form having a specific pharmaceutical can vary. In some instances, the use of permeation enhancer in making a polymer matrix dosage form will result in good or even excellent absorption for one pharmaceutical, may result in no or relatively low enhancement when another pharmaceutical is used. Use of combinations of two or more of the skin permeation enhancer compounds frequently result in superior results, such as greater transdermal absorption.

Specific skin permeation enhancers which can be used in making the polymer matrix dosage forms of this invention include saturated and unsaturated fatty acids and their esters, alcohols, monoglycerides, acetate, diethanolamides and N, N-dimethylamides, such as oleic acid, propyl oleate, oleyl acetate, propyl or isopropyl myristate, myristyl alcohol, myristyl N, N-dimethyl amide, stearic acid and stearyl alcohol, stearyl propyl ester, monostearin, capryl alcohol, ethyl caprylate, hexamethylene lauramide, hexamethylene palmitate, esters, alcohols, and acids in which the carbon chain thereof is $CH_3(CH_2)_n$—C—, wherein n has 4–16 carbon atoms and combinations of them with, for example, 1-dodecylazacycloheptan-2-one sold under the trademark Azone by Nelson Research and Development; decyl methyl sulfoxide, dimethyl sulfoxide, salicylic acid and derivatives, N,N-diethyl-m-toluamide, crotamiton, 1-substituted azacycloalkan-2-ones such as disclosed in U.S. Pat. No. 4,316,893 (the 1-substitnent having 0–17 carbon atoms, preferably, 1–11 carbon atoms), and various other compounds which are biologically compatible and have transdermal permeation activity.

The following examples are in illustration of the invention and are not intended to be limiting.

EXAMPLE 1

The following ingredients are used in making the pharmaceutical-containing polymer matrix discs: hydromorphone, 10 parts; DC-360 polysiloxane medical fluid (20 cps), 10 parts; silicone (medical-grade) 382 elastomer, 80 parts; catalyst M, 20 drops per 100 g. of the mixture.

The hydromorphone is thoroughly dispersed in the 80 parts of Silastic medical-grade 382 elastomer by using a high torque mixer (sold by Cole-Parmer Company) at about 1000 RPM.

With continued agitation, 20 parts of DC-360 (silicone medical fluid) and 20 drops (for every 100 g of the mixture) of a cross-linking agent, designated as catalyst M, which is stannous octanoate, are added to the hydromorphone-elastomer microdispersed mixture. After each addition of the mixture, material is thoroughly mixed, and the dispersed mixture is placed under vacuum to remove entrapped air.

The hydromorphone-polydimethylsiloxane dispersion is placed into a device maker and is cross-linked at an elevated temperature (25°–100° C.) to form a cross-linked, medicated polymer sheet, which has a thickness of 0.2–3 mm.

The medicated polymer sheet is removed from the device maker and is cut into circular discs of about 3–20 sq. cm. The discs are attached to a backing layer of heat sealable polyester film which is laminated to aluminum foil. This laminate is sold by 3M Company as Scotchpak 1006. The medicated discs are attached using an adhesive polymer solution, which is a silicone adhesive polymer sold by Dow Corning as DC-355. Alternately, the discs can be formed directly on the backing layer and in practice are.

The silicone adhesive is believed to have the following structure:

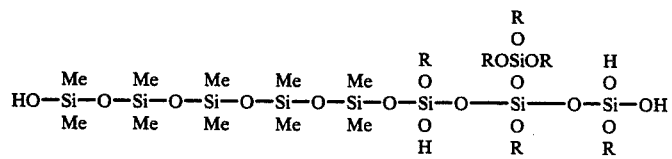

The skin permeation enhancer-adhesive film is made using the following ingredients: skin permeation enhancer, 6.5 parts; acetone 30 parts; and adhesive polymer solution, 100 parts. The skin permeation enhancer-adhesive layer is made by dissolving the 6.5 parts by weight of a skin permeation enhancer in 30 parts of acetone. The acetone solution then is added to 100 parts of a silicone adhesive solution sold by Dow-Corning under the designation DC-355.

The mixture is thoroughly mixed to form a homogeneous mixture of skin permeation enhancer and adhesive polymer, which is applied to a strip of a release liner which is a siliconized, or a Teflon-coated polyester film to permit easy removal of the release liner just prior to application of the final polymer matrix disc dosage unit to the subject to be transdermally treated. The adhesive mixture is applied at a controlled thickness. The formed layer has a thickness of about 50–200 microns. The layer is dried completely in vacuum to remove volatile matter.

The skin permeation enhancer-adhesive polymer layer with release liner is applied onto the hydromorphone-containing polymer matrix disc with the attached backing layer under a constant pressure to provide a firmly adhered strip of a four-layered structure as follows:
1. Backing layer
2. Hydromorphone-containing polymer matrix layer
3. Skin permeation enhancer-adhesive layer
4. Release film layer which can be readily removed to permit application to the skin of the subject to receive transdermally the hydromorphone.

By use of an appropriate cutter, the strip is cut to provide the transdermal hydromorphone polymer matrix dosage units which are circular in shape and have an area of about 10 sq. cm.

The above polymer matrix disc dosage units are made using the following skin permeation enhancers: 1-dodecylazacycloheptan-2-one (sold under the trademark Azone), propyl myristate and propyl oleate.

The transdermal absorption of the hydromorphone from the polymer matrix dosage units of this invention is evaluated by using a skin specimen from a "hairless" mouse or human cadaver by following the procedure described by P. R. Keshary and Y. W. Chien, in Drug Develop. & Ind. Pharm., 10 (6) 883–913 (1984).

Transdermal polymer matrix dosage units are obtained and evaluated as shown in Tables I and II.

TABLE I

TRANSDERMAL ABSORPTION FROM POLYMER MATRIX DISC DOSAGE UNITS OF HYDROMORPHONE

| Enhancers (3.2 MG/CM$^2$) | Normalized Permeation Rate (MCG/CM$^2$/HR ± S.D.) | Enhancing Factors |
|---|---|---|
| None | 0.103 ± 0.022 | 1.00 |
| Propyl Myristate | 0.41 ± 0.11 | 3.98 |
| Propyl Oleate | 0.37 ± 0.098 | 3.59 |
| 1-Docecylazacycloheptan-2-One | 0.94 ± 0.35 | 9.13 |

TABLE II

TRANSDERMAL ABSORPTION OF HYDROMORPHONE FROM POLYMER MATRIX DISC DOSAGE UNITS CONTAINING DECYL METHYL SULFOXIDE AS SKIN ABSORPTION ENHANCER

| Enhancer Concentration (MG/CM$^2$) | Permeation Rate (MCG/CM$^2$/HR ± S.D.) | Enhancing Factors |
|---|---|---|
| 0 | 0.103 ± 0.022 | 1.00 |
| 5 | 0.43 ± 0.008 | 4.17 |
| 10 | 0.95 ± 0.22 | 9.22 |

EXAMPLE 2

Figure 3:
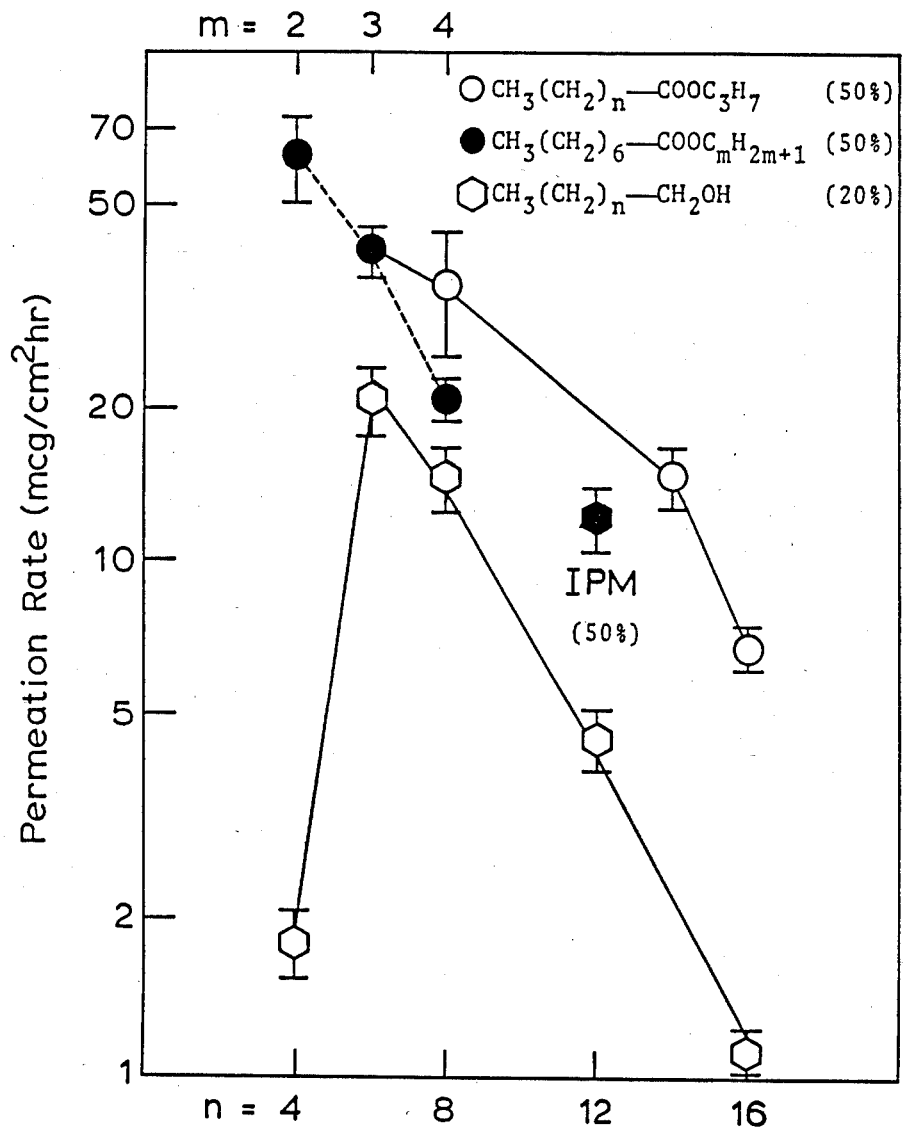
FIG. 3 is a graph showing permeation rates (mcg/cm$^2$ hr) from dosage units in which the polymer matrix layer has 10% (w/w) of hydromorphone and various concentrations of different skin permeation enhancing agents.
Figure 4:
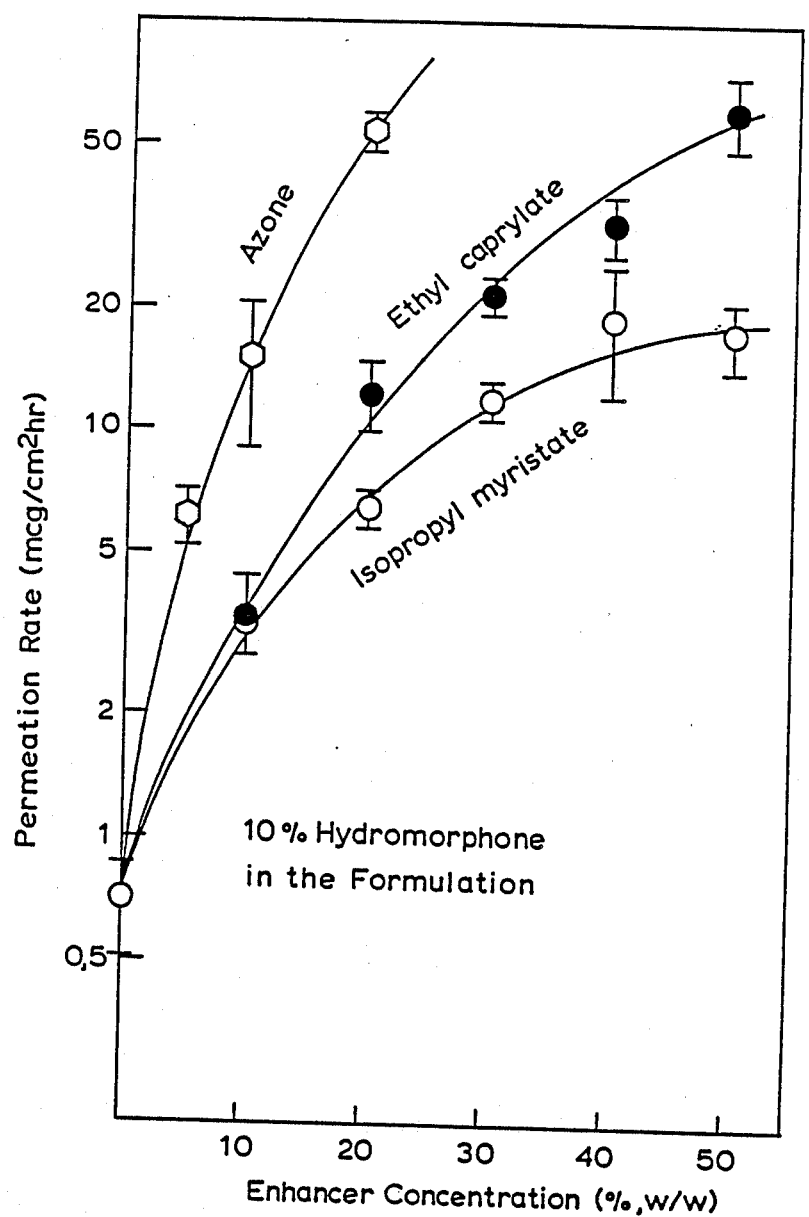
FIG. 4 is a graph showing permeation rates (mcg/cm$^2$ hr) from dosage units in which the polymer matrix layer has 10% (w/w) of hydromorphone and various concentrations of different skin permeation enhancing agents.
Figure 5:
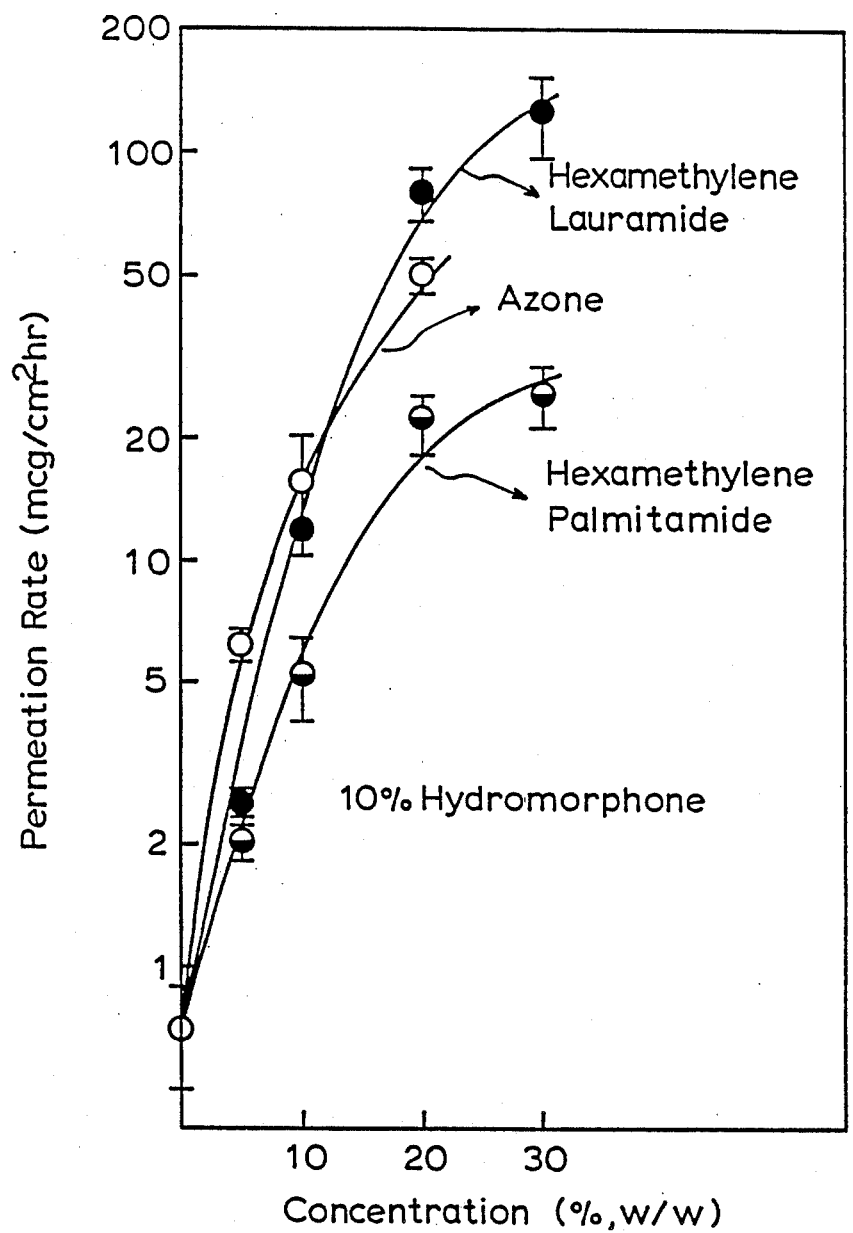
FIG. 5 is a graph showing permeation rates (mcg/cm$^2$ hr) from dosage units in which the polymer matrix layer has 10% (w/w) of hydromorphone and various concentrations of different skin permeation enhancing agents.
Figure 6:
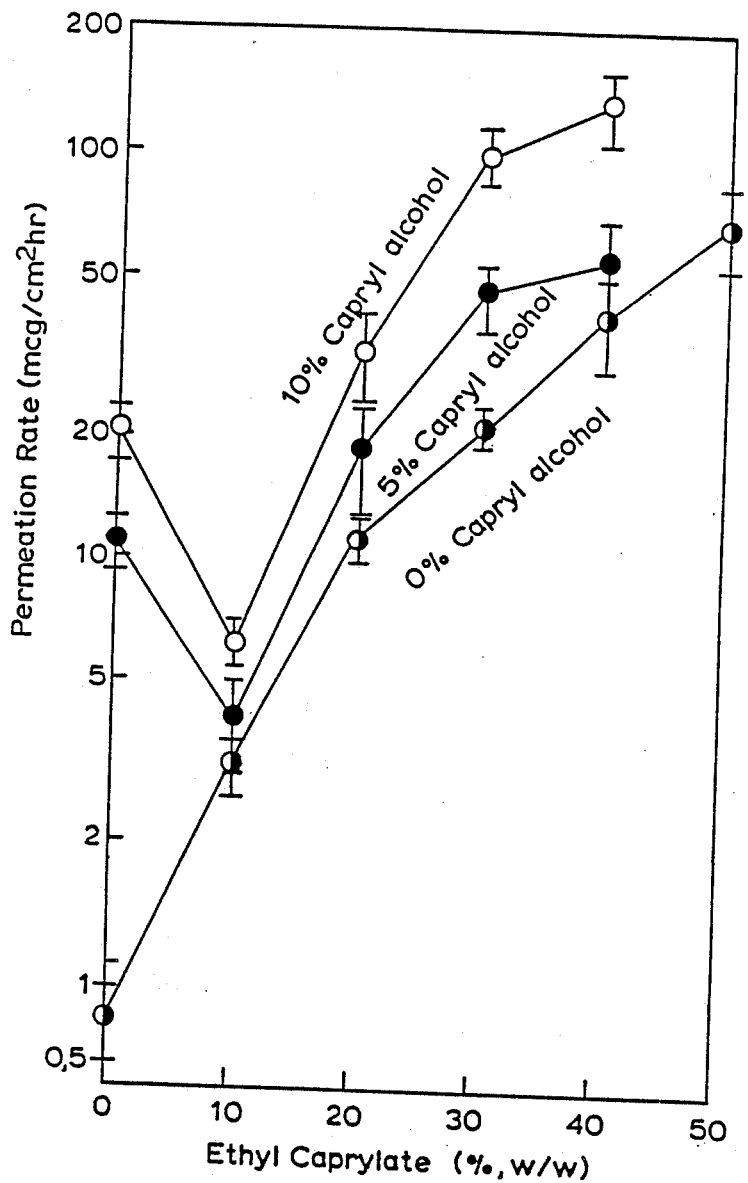
FIG. 6 is a graph showing permeation rates (mcg/cm$^2$ hr) from dosage units in which the polymer matrix layer has 10% (w/w) of hydromorphone with various concentrations of ethyl caprylate alone or in combination with other skin permeation enhancing agents.

The general procedure as outlined in Example 1 is followed to provide the polymer matrix dosage units described in FIGS. 2–6 and in the following TABLES. The dosage units are square shaped with rounded corners having a surface area of about 10 cm$^2$. The skin permeation enhancing agents are mixed thoroughly with the hydromorphone prior to the addition of the mixture of the pharmaceutical and the dispersing agent. The skin permeation enhancing agent can alternatively be thoroughly mixed with the polymer prior to the addition thereto of pharmaceutical and dispersing agent, if the enhancing agent is not employed as the dispersing agent. A separate polyurethane overlay adhesive means is used to adhere the dosage unit to the subject being treated. Just prior to use, a peelable layer is removed from the overlay to expose an adhesive layer which overlays the polymer matrix layer (bearing a backing layer) and adheres the surface of the matrix layer to the skin of the subject being treated. In FIG. 3, m is an integer of 1 to 8.

TABLE III

DEPENDENCE OF PERMEATION RATES ON THE AZONE CONCENTRATION IN THE MATRIX AND IN THE ADHESIVE LAYERS

| Matrix | | Adhesive | |
|---|---|---|---|
| Hydromorphone (%, w/w) | Azone (%, w/w) | Azone (%, v/v) | Permeation Rate (mcg/cm$^2$ hr) |
| 10 | 5 | — | 6.34 ± 0.76 |
| 10 | 5 | 5 | 3.58 ± 0.57 |
| 10 | 5 | 10 | 5.54 ± 0.57 |
| 10 | 5 | 20 | 9.82 ± 1.95 |
| 10 | 10 | — | 14.76 ± 6.04 |
| 10 | 10 | 5 | 5.06 ± 0.90 |
| 10 | 10 | 10 | 7.14 ± 0.13 |
| 10 | 10 | 20 | 9.28 ± 0.90 |
| 10 | 20 | — | 53.94 ± 2.28 |
| 10 | 20 | 5 | 22.47 ± 5.50 |
| 10 | 20 | 10 | 27.47 ± 4.42 |
| 10 | 20 | 20 | 34.79 ± 4.09 |

TABLE IV

DEPENDENCE OF PERMEATION RATES ON THE ISOPROPYL MYRISTATE (IPM) CONCENTRATIONS IN THE MATRIX AND IN THE ADHESIVE LAYERS

| Matrix | | Adhesive | |
|---|---|---|---|
| Hydromorphone (%, w/w) | Azone (%, w/w) | Azone (%, v/v) | Permeation Rate (mcg/cm$^2$ hr) |
| 10 | 10 | — | 3.64 ± 0.82 |
| 10 | 10 | 25 | 2.63 ± 0.23 |
| 10 | 10 | 50 | 3.25 ± 0.60 |
| 10 | 20 | — | 6.49 ± 0.68 |
| 10 | 20 | 25 | 8.39 ± 1.67 |
| 10 | 20 | 50 | 8.04 ± 2.02 |
| 10 | 30 | — | 12.09 ± 1.16 |
| 10 | 30 | 25 | 9.95 ± 1.79 |
| 10 | 30 | 30 | 11.80 ± 3.52 |
| 10 | 40 | — | 18.48 ± 7.00 |
| 10 | 40 | 25 | 16.26 ± 0.86 |
| 10 | 40 | 50 | 19.37 ± 1.75 |
| 10 | 50 | — | 17.87 ± 3.56 |
| 10 | 50 | 25 | 16.33 ± 1.95 |
| 10 | 50 | 50 | 19.48 ± 2.18 |

EXAMPLE 3

The general procedure of Example 1 is repeated. The skin permeation enhancing agent ethyl caprylate is used in the amount of 50 percent based on the polymer weight, as the dispersing agent. Hydromorphone concentration used is 10 percent based on the weight of the polymer used in making the matrix layer.

A second group of polymer matrix dosage units are made using a combination of two skin permeation enhancing agents as the dispersant, 30 pecent of ethyl caprylate and 5 percent of capryl alcohol.

In neither instance is an adhesive layer present as a layer on the surface of the polymer matrix but rather is applied to a ring of the backing layer made by shaping the backing layer around the edges of the polymer matrix layer and then generally extending the backing layer in a direction planar to the surface of the polymer matrix layer for a distance of about 0.5–1.0 cm. to this backing surface, a ring of adhesive using the adhesive and procedure of Example 1 is used (no skin permeation enhancing agent is used in the adhesive layer). The adhesive ring has a width of about 0.4–0.8 cm. The adhesive ring is spaced from the polymer of the matrix layer to preclude any migration of skin permeation enhancing agent.

EXAMPLE 4

The procedures of Examples 1–3 are repeated using the following morphinan narcotic pharmaceuticals: levorphanol, methopon, oxymorphone, morphine, buprenorphine, diprenorphine, butorphanol, levallorphan, nalorphine, naloxone, nalbuphine, oxilorphan, nalmexone, ketobemidone, profadol, cyclorphan, cyprenorphine, desomorphine, dihydromorphine, 3-hydroxy-N-methylmorphinan, levophenacylmorphan, norlevorphanol, phenomorphan, pholodine, hydroxypethidine, naltrexone, apomorphine and codeine. The dose loadings are adjusted to provide desired transdermal absorption dosages.

The procedures of Examples 1–3 are also repeated using the silicone polymer MDX4-4210, which has methylvinyl siloxane groups and the matrix is cross-linked using a two-stage platinum catalyst.

What is claimed is:

1. A transdermal morphinan narcotic analgesic or antagonist pharmaceutical polymer matrix dosage unit comprising:
   (a) a backing layer which is substantially impervious to said pharmaceutical to be delivered transdermally; and
   (b) a polymer matrix disc layer which is adhered to said backing layer and which has microdispersed therein effective dosage amounts of one or more pharmaceuticals selected from the group consisting of morphinan narcotic analgestic and antagonist pharmaceuticals, said polymer being bioacceptable and permitting said pharmaceuticals to be transmitted for transdermal absorption, said pharmaceuticals being stable in said polymer matrix and being transdermally absorbed simultaneously to provide at least minimum effective daily doses of said pharmaceuticals.

2. A transdermal polymer matrix dosage unit of claim 1 wherein said polymer matrix layer has dispersed therein an effective amount of one or more skin permeation enhancing agents.

3. A transdermal dosage unit of claim 1 wherein the polymer matrix is a silicon polymer or copolymer.

4. A transdermal polymer matrix dosage unit of claim 3 wherein the silicon polymer or copolymer is a methyl silicone polymer or copolymer or methylvinyl silicone polymer or copolymer.

5. A transdermal polymer matrix dosage unit of claim 1 wherein the polymer matrix disc layer is a crosslinked polysiloxane polymer of the following formula:

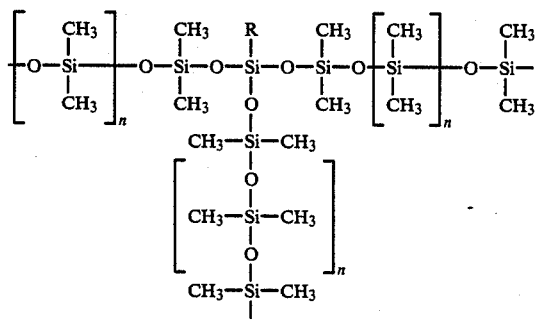

wherein R is alkyl or alkoxy having 1-7 carbon atoms, vinyl, phenyl or combination thereof; and wherein n is about 100 to about 5,000.

6. A transdermal polymer matrix dosage unit of claim 3 wherein the matrix is made up of microdispersed compartments having a cross-sectional dimension of from about 10 to about 200 microns.

7. A transdermal polymer matrix dosage unit of claim 1 wherein the pharmaceutical is hydromorphone.

8. A transdermal polymer matrix dosage unit of claim 7 wherein the hydromorphone is present in the polymer matrix layer in a loading amount of at least about 10 percent by weight based on the matrix polymer weight.

9. A transdermal polymer matrix dosage unit of claim 7 wherein the hydromorphone is present in the polymer matrix layer in a loading amount of about 10 percent by weight based on the matrix polymer weight.

10. A transdermal polymer matrix dosage unit of claim 1 wherein an effective dosage of at least about 1.2 mg of said pharmaceutical is transdermally delivered in a 24-hour period.

11. A transdermal polymer matrix dosage unit of claim 10 wherein the pharmaceutical is hydromorphone.

12. A transdermal polymer matrix dosage unit of claim 11 wherein the hydromorphone is transdermally delivered in an amount of at least 2.4 mg in a 24-hour period.

13. A transdermal polymer matrix dosage unit of claim 3 wherein the silicone polymer is a cross-linked siloxane polymer and the pharmaceutical hydromorphone is transdermally delivered in an amount of at least 1.2 mg in a 24-hour period.

14. A transdermal polymer matrix dosage unit of claim 13 wherein the amount transdermally delivered is at least 2.4 mg in a 24-hour period.

15. A transdermal polymer matrix dosage unit of claim 13 wherein the cross-linked silicone polymer is polydimethylsiloxane.

16. A transdermal polymer matrix dosage unit of claim 13 wherein the cross-linked silicone polymer is a crosslinked methylvinyl silicone polymer.

17. A transdermal polymer matrix dosage unit of claim 13 wherein the skin permeation enhancing agent present in the matrix layer or adhesive layer or both layers and is selected from the group consisting of isopropyl myristate, saturated fatty acids having the structure $CH_3(CH_2)_nCOOH$ wherein n is an integer of 4 to 16, saturated alcohols having the structure $CH_3(CH_2)_nCH_2OH$ wherein n is an integer of 4 to 16, azone, ethyl caprylate, hexamethylene lauramide, hexamethylene palmitamide, and combinations of ethyl caprylate and capryl alcohol.

18. A transdermal dosage unit of claim 17 wherein the skin permeation enhancing agent is azone.

19. A transdermal dosage unit of claim 17 wherein the skin permeation agent is isopropyl myristate.

20. A transdermal dosage unit of claim 17 wherein the skin permeation agent is ethyl caprylate.

21. A transdermal dosage unit of claim 17 wherein the skin permeation agent is a combination of ethyl caprylate and capryl alcohol.

22. A process of administering an effective dose amount of a morphinan narcotic analgesic or antagonist pharmaceutical by applying a dosage unit as described in claim 1.

23. A process of claim 22 wherein the pharmaceutical is hydromorphone.

24. A dosage unit of claim 1 wherein the morphinan pharmaceutical is selected from the group consisting of hydromorphone, oxymorphone, buprenorphine, diprenorphine, butorphanol, levallorphan, nalorphine, naloxone, nalbuphine, oxilorphan, nalmexone, naltrexone, ketobemidone, apocodeine, profadol, cyclorphan, cyprenorphine, desomorphine, dihydromorphine, 3-hydroxy-N-methylmorphinan, levophenacylmorphinan, norlevorphanol, oxymorphone, phenomorphan, pholcodine, hydroxypethidine, apomorphine, codeine, morphine and hydrocodone.

25. A dosage unit of claim 22 wherein said polymer matrix layer has dispersed therein an effective amount of one or more skin permeation enhancing agents.

* * * * *